(12) United States Patent
Wang et al.

(10) Patent No.: US 9,408,556 B2
(45) Date of Patent: Aug. 9, 2016

(54) INTEGRATED ANALYSIS DEVICE FOR SIMULTANEOUSLY DETECTING EBCS AND VOCS IN HUMAN EXHALED BREATH

(75) Inventors: Ping Wang, Zhejiang (CN); Di Wang, Zhejiang (CN); Le Wang, Zhejiang (CN); Jin Yu, Zhejiang (CN); Kai Yu, Zhejiang (CN); Yishan Wang, Zhejiang (CN); Lin Wang, Zhejiang (CN); Cong Zhao, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 555 days.

(21) Appl. No.: 13/990,007

(22) PCT Filed: Dec. 1, 2010

(86) PCT No.: PCT/CN2010/079318
§ 371 (c)(1),
(2), (4) Date: May 28, 2013

(87) PCT Pub. No.: WO2012/071716
PCT Pub. Date: Jun. 7, 2012

(65) Prior Publication Data
US 2013/0253360 A1    Sep. 26, 2013

(51) Int. Cl.
*A61B 5/08* (2006.01)
*G01N 33/00* (2006.01)
*G01N 33/497* (2006.01)
*A61B 5/097* (2006.01)

(52) U.S. Cl.
CPC ............ *A61B 5/082* (2013.01); *A61B 5/097* (2013.01); *G01N 33/0047* (2013.01); *G01N 33/497* (2013.01)

(58) Field of Classification Search
CPC .... A61B 5/082; A61B 5/097; G01N 33/0047; G01N 33/497
See application file for complete search history.

(56) References Cited

U.S. PATENT DOCUMENTS

2009/0275852 A1* 11/2009 Oki .................... A61B 5/097
600/532
2010/0268106 A1 10/2010 Johnson et al.

OTHER PUBLICATIONS

Liu, Q., Cai, H., Xu, Y., Xiao, L., Yang, M., Wang, P., "Detection of heavy metal toxicity using cardiac cell-based biosensor", Mar. 12, 2007, Biosensors and Bioelectronics, pp. 3224-3229.*

(Continued)

*Primary Examiner* — Christian Jang
(74) *Attorney, Agent, or Firm* — James Stipek; John Bednarz; Polsinelli PC (57) ABSTRACT

The present embodiments disclose a device including a module for sampling, separating and enriching a detected object, an exhaled breath condensates (EBCs) detection module and a combined volatile organic compounds (VOCs) detection module. The sampling module is connected with the EBCs detection module via a syringe pump for sample injection and is connected with the combined VOCs detection module by a capillary separation column. EBCs and VOCs in human exhaled breath are simultaneously sampled, separated and condensed; the heavy metal ions, cell factors, etc. in the collected EBCs are detected with a light addressable potentiometric sensor (LAPS); the condensed VOCs can be quantitatively detected by the combined VOCs detection module with a high sensitivity; and a heating rod and a platinum resistor can be conveniently replaced because a separated outlet heating piece is designed in the combined VOCs detection module.

8 Claims, 5 Drawing Sheets

(56) References Cited

OTHER PUBLICATIONS

Wild, D., "The Immunoassay Handbook" 3rd edition, 2005, pp. 300-301.*
CN101657710A, publication date Feb. 24, 2010, China, English translation of Abstract only, one page.
CN101742964A, publication date Jun. 16, 2010, China, English translation of Abstract only, one page.
CN201289439Y, publication date Aug. 12, 2009, China, English translation of Abstract only, one page.
International Search Report regarding PCT/CN2010/079318, dated Sep. 15, 2011, 3 pages.

* cited by examiner

INTEGRATED ANALYSIS DEVICE FOR SIMULTANEOUSLY DETECTING EBCS AND VOCS IN HUMAN EXHALED BREATH

FIELD OF THE INVENTION

The present invention relates to an integrated analysis device for simultaneously detecting human exhaled breath condensates (EBCs) and volatile organic compounds (VOCs) in exhaled breath, and in particular, to an integrated analysis device in which a light addressable potentiometric sensor (LAPS) is employed to detect EBCs, a simultaneous sampling, separation and condensation of EBCs and VOCs from human exhaled breath can be achieved, and a VOC detection module with an combined structure is employed.

BACKGROUND OF THE INVENTION

Recently, human exhaled breath has been widely studied around the world, and these words primarily focus on the relevance of EBCs and VOCs in exhaled breath to human diseases.

To study EBCs and VOCs in exhaled breath, the first step is to collect these two study objects. With regard to a device for collecting EBCs, there are relevant studies around the world, and there already have been some commercialized instruments and devices, which principles rely on that exhaled breath is first passed through a condensation tube, and then the liquid EBCs are collected. Therein, for some devices the cost of detection is increased due to the condensation tube being disposable, and for some other devices the flexibility in application is insufficient due to their large-sized cooler.

Currently, there is no unified standard for the device for collecting VOCs in human exhaled breath, however, there already have been some relevant studies. In a VOCs gas collecting device developed by Michael Phillips, USA, exhaled breath is first blew into one end of a gas container by a disposable mouthpiece, wherein the other end of the gas container is connected to an adsorption tube, the gases in the container are drawn out by the adsorption tube through the other end of the pump, and thus the VOCs in the exhaled breath are captured by the adsorption tube. This device is comparatively automated, however, it takes into account neither the adsorption of the VOCs by the container and other connecting pieces, nor the adsorption temperature of the adsorption tube in every sampling process.

Furthermore, nowadays internationally the existing devices can only collect either EBCs or VOCs, and internationally there is a lack of device which can collect EBCs and VOCs simultaneously, and there is also no report about the studies of integrating two sets of collecting methods into one instrument and performing a subsequent analysis and detection.

To obtain EBCs, exhaled breath is introduced into a cooling system, and water vapor is condensed into liquid by means of a low temperature. EBCs contain water vapor, adenosine, hydrogen peroxide, ions, nitric oxide, prostaglandins, protein and nucleic acid, etc. which are brought out from the lung and the respiratory tract. With the features of simple to collect, non-invasive, acceptable to patients, etc., EBCs may become a new approach for finding the early diagnosis of lung cancer, screening of high-risk groups, etc. However, current common detection means are general immunological methods of which the detection speed is low, the process is complex, and the sensitivity is not high.

A surface acoustic wave (SAW) gas sensor has been widely applied in gas detection. However, since its characteristics are influenced by many environmental factors (such as gas flow, temperature, etc.) and the area of its sensitive region is relatively small so that it is difficult for chemical substances to be fully adsorbed to the sensor surface, its characteristic of high sensitivity cannot be completely achieved. If the working environmental conditions of the SAW gas sensor are not strictly controlled, the goal of rapidly detecting chemical substances with low trace concentrations in human exhaled breath cannot be achieved. A heating rod and a platinum resistor directly inserted in the traditional outlet heating piece of capillary will expand by heat after use, and get stuck in the heating piece, which makes it difficult to replace them.

SUMMARY OF THE INVENTION

An object of the present invention is to provide an integrated analysis device for simultaneously detecting EBCs and VOCs in human exhaled breath considering the deficiencies of the internationally existing research methods and devices.

The object of the present invention is achieved by the following solution: an integrated analysis device for simultaneously detecting EBCs and VOCs in human exhaled breath comprises a module for sampling, separating and enriching a detected object, an EBCs detection module and a combined VOCs detection module; the module for sampling, separating and enriching a detected object is connected with the EBCs detection module via a syringe pump for sample injection, and the module for sampling, separating and enriching a detected object is connected with the combined VOCs detection module via a capillary separation column.

Therein, the EBCs detection module comprises an EBC inlet, an inlet for washing liquid, a first three-way valve, a composite light addressable potentiometric sensor (LAPS) sensor for heavy metal ions, a first working electrode, a light source controlled by a signal generating circuit, a reference electrode, a second three-way valve, a urea inlet, a detecting electrode, a carcinoembryonic antigen light addressable potentiometric sensor (CEA-LAPS), a second working electrode, a $Cr^{3+}$ ion detecting cavity and a CEA detecting cavity; the EBC inlet, the inlet for washing liquid and the $Cr^{3+}$ ion detecting cavity are connected via the first three-way valve, the urea inlet, the $Cr^{3+}$ ion detecting cavity and the CEA detecting cavity are connected via the second three-way valve, the reference electrode is inserted into the $Cr^{3+}$ ion detecting cavity from its top, the composite LAPS sensor for heavy metal ions and the first working electrode are fixed to the bottom of the $Cr^{3+}$ ion detecting cavity, the first working electrode is joined with the bottom of the composite LAPS sensor for heavy metal ions, the detecting electrode is inserted into the CEA detecting cavity from its top, the CEA-LAPS and the second working electrode are fixed to the bottom of the CEA detecting cavity, and the second working electrode is joined with the bottom of the CEA-LAPS sensor. An inlet for CEA antibody-urease compound liquid and an outlet for waste liquid are disposed at the upper portion of the CEA detecting cavity. One light source controlled by a signal generating circuit is placed at a position corresponding to the composite LAPS sensor for heavy metal ions under the $Cr^{3+}$ ion detecting cavity, and another light source controlled by a signal generating circuit is placed at a position corresponding to the CEA-LAPS sensor under the CEA detecting cavity.

Furthermore, the CEA-LAPS sensor is built by depositing a $SiO_2$ layer and a $Si_3N_4$ film in turn on a Si substrate by the chemical vapor deposition and the photolithography, and a nanolayer and a biotin layer on the surface of the $Si_3N_4$ film are formed by a chemical coating method.

Compared to the prior art, the present invention has the following technical effects:

1. In the method and the integrated analysis device for simultaneously detecting EBCs and VOCs in human exhaled breath provided by the present invention, it is achieved that EBCs and VOCs in human exhaled breath are simultaneously sampled, separated and enriched; substances in the collected EBCs (such as heavy metal ions, cell factors, etc.) are detected with the LAPS; and the enriched VOCs can be quantitatively detected via the combined VOCs detection module with a high sensitivity.

2. The EBCs detection module includes two test cavities and two LAPS sensors which perform a simultaneous detection of $Cr^{3+}$ and CEA in EBCs. In the first test cavity, one LAPS sensor with surface modification by heavy metal ion (e.g. $Cr^{3+}$) sensitive materials performs the detection of $Cr^{3+}$; in the second test cavity, the other LAPS immune sensor successively modified by nanometer material, biotin-avidin and CEA antibody, in which the CEA antibody, the target antigen CEA, and the added CEA antibody-urease compound form a dual antibody sandwich structure and altering the concentration of $H^+$ by decomposing urea by the urease, thereby realizing the detection of the CEA concentration. At the back of the two LAPS sensors two light sources with different frequencies are employed to excite the sensor cells of $Cr^{3+}$ and CEA respectively, thereby realizing a simultaneous detection of $Cr^{3+}$ and CEA in exhaled breath condensates with two sensors of the same detection module.

3. In the module for sampling, separating and enriching a detected object integrates a gas path construction for collecting the EBCs and enriching the VOCs in exhaled breath, and the automated sampling and injection are achieved for the subsequent detection; this method utilizes an innovative cooling measure so as to realize the automated collecting and cleaning while guaranteeing the efficiency of collecting the exhaled breath condensates, and to effectively reduce the weight and volume of the condensation system; and this method ensures that less exhaled breath is left over in the pipeline, and the breath from anatomical dead space in medicine is effectively removed during the enrichment of VOCs.

4. The VOCs detection module employs a combined gas detection head structure, in which a snap-fit gas chamber makes the capillary outlet aim to the sensitive region of the gas sensor accurately, thereby ensuring that the VOCs in the sample are efficiently adsorbed by the gas sensor. The design of the gas chamber leads the sensor to work in a relatively closed room, which decreases the influence of the environmental gas flow on the gas sensor, and an observation window is disposed around the gas chamber so that the working condition of the sensor is observed. Below the sensor, there is a semiconductor cooling plate which can accurately control the working temperature of the sensor, and reduce the influence of the temperature characteristics of the sensor on the detection of VOCs. The design of a separated outlet heating piece in the detection head may facilitate the replacement of heating rod and platinum resistor.

In the drawings:
1 disposable mouthpiece
2 saliva collector
3 inspiration check valve
4 expiration check valve
5 first three-way solenoid valve
6 second three-way solenoid valve
7 activated carbon filter
8 inlet check valve
9 gas buffering chamber
10 third three-way solenoid valve
11 gas outlet
12 adsorption tube
13 miniature vacuum pump
14 gas mass flow meter
15 linear stepping motor
16 piston
17 washing liquid storage for condensation tube
18 peristaltic pump
19 condensation module
20 condensate collector
21 heating rod
22 heating piece
23 conduit
24 aluminium piece
25 cooling plate
26 gas inlet
27 inlet for washing liquid
28 condensation tube
29 ice cooling box
30 condensate outlet
31 outlet heating piece
32 gas nozzle
33 upper cover of sensor gas-chamber
34 heat sink
35 conduit for capillary extraction
36 first perforation for hanging and fixing
37 first screw perforation for heating piece incorporating
38 second screw perforation for heating piece incorporating
39 first pin perforation for heating piece
40 second pin perforation for heating piece
41 cambered guiding groove for capillary
42 third pin perforation for heating piece
43 second perforation for hanging and fixing 44 fourth pin perforation for heating piece
45 slot for heating rod
46 slot for platinum resistor
47 first insertion screw hole
48 second insertion screw hole
49 gas chamber fixing hole
50 gas chamber top hole
51 first gas chamber closing hole
52 observation hole
53 groove for cooling plate
54 groove for the lead wire of cooling plate
55 gas chamber embedding groove
56 second gas chamber closing hole
57 EBC inlet
58 inlet for washing liquid
59 first three-way valve
60 composite LAPS sensor for heavy metal ions
61 first working electrode
62 light source controlled by a signal generating circuit
63 reference electrode
64 second three-way valve
65 urea inlet
66 inlet for CEA antibody-urease compounds
67 detecting electrode
68 CEA-LAPS sensor
69 second working electrode
70 outlet for waste liquid
71 bias voltage
72 Si substrate
73 $SiO_2$ layer
74 $Si_3N_4$ layer
75 nanolayer
76 biotin layer
77 CEA antigen
78 CEA antibody-urease
79 CEA antibody-avidin.

DETAILED DESCRIPTION OF THE INVENTION

In the following the present invention will be further described in connection with the drawings and embodiments, and the objects and effects of the present invention will become more apparent.

Figure 1:
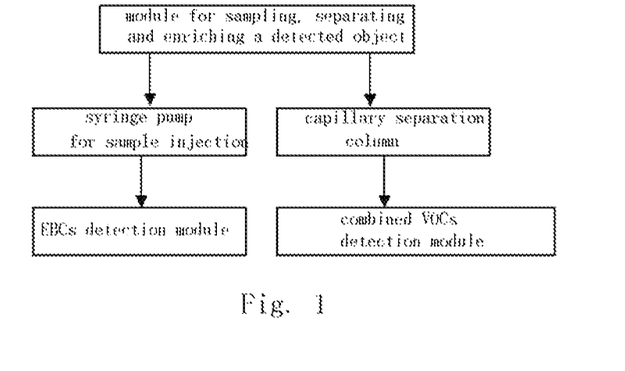
FIG. 1 is a system structure block diagram of an integrated device for detecting EBCs and VOCs in human exhaled breath.

As shown in FIG. 1, an integrated analysis device for simultaneously detecting EBCs and VOCs in human exhaled breath of the present invention comprises a module for sampling, separating and enriching a detected object, an EBCs detection module and a combined VOCs detection module. Therein, the module for sampling, separating and enriching a detected object is connected with the EBCs detection module via a syringe pump for sample injection, and the module for sampling, separating and enriching a detected object is connected with the combined VOCs detection module via a capillary separation column.

Exhaled breath sample is blown into the module for sampling, separating and enriching a detected object by a person, and after the saliva is filtered, the EBCs are collected and the VOCs are enriched in two sets of pipelines. The collected EBCs come into the EBCs detection module via the syringe pump for sample injection, and the concentrations of $Cr^{3+}$ ions and CEA in the EBCs are directly measured. The enriched VOCs are separated in the capillary separation column, and passed into the combined VOCs detection module with a gas sensor whose working conditions are strictly controlled, thereby realizing a detection with a high sensitivity.

Figure 2:
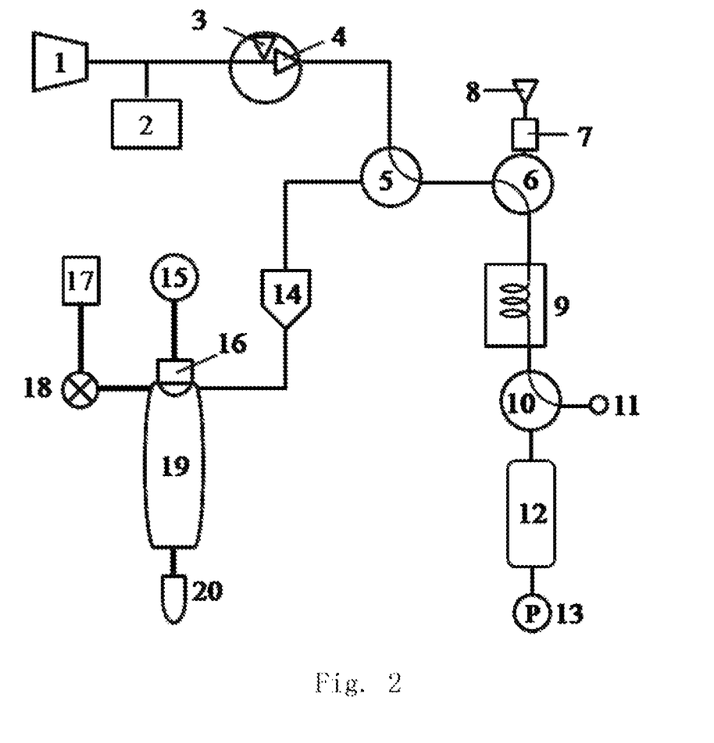
FIG. 2 is a working process in which a module for sampling, separating and enriching a detected object collects a particular portion of the exhaled breath.
Figure 3:
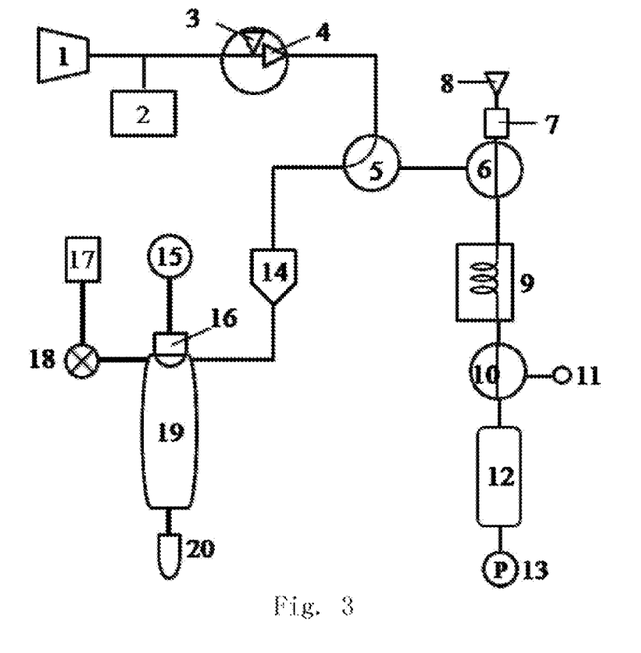
FIG. 3 is a working process in which a module for sampling, separating and enriching a detected object collects EBCs and enriches VOCs from the exhaled breath.

As shown in FIGS. 2 and 3, the module for sampling, separating and enriching a detected object comprises a mouthpiece 1, a saliva collector 2, an inspiration check valve 3, an expiration check valve 4, a first three-way solenoid valve 5, a second three-way solenoid valve 6, an activated carbon filter 7, an inlet check valve 8, a gas buffering chamber 9, a third three-way solenoid valve 10, a gas outlet 11, an adsorption tube 12, a miniature vacuum pump 13, a gas mass flow meter 14, a linear stepping motor 15, a piston 16, a washing liquid storage for condensation tube 17, a peristaltic pump 18, a condensation module 19, and a condensate collector 20.

Therein, the mouthpiece 1 is connected with the first three-way solenoid valve 5 via the inspiration check valve 3 and the expiration check valve 4 in turn, the saliva collector 2 is connected between the mouthpiece 1 and the inspiration check valve 3, the two outlets of the first three-way solenoid valve 5 are connected respectively with the second three-way solenoid valve 6 and the gas mass flow meter 14, the inlet check valve 8 is then connected with the third three-way solenoid valve 10 via the activated carbon filter 7, the second three-way solenoid valve 6 and the gas buffering chamber 9 in turn, the two outlets of the third three-way solenoid valve 10 are then connected respectively with the gas outlet 11 and with the adsorption tube 12 to the miniature vacuum pump 13, the gas mass flow meter 14 is connected with the condensation module 19, and all the above connections are gas pipeline connections. The washing liquid storage for condensation tube 17 is connected with the condensate collector 20 in a liquid pipeline via the peristaltic pump 18 and the condensation module 19 in turn. The linear stepping motor 15 is connected with the piston 16, and drives the piston 16 into the condensation module 19.

FIG. 2 shows a working process in which the module for sampling, separating and enriching a detected object collects a particular portion of the exhaled breath.

Figure 4:
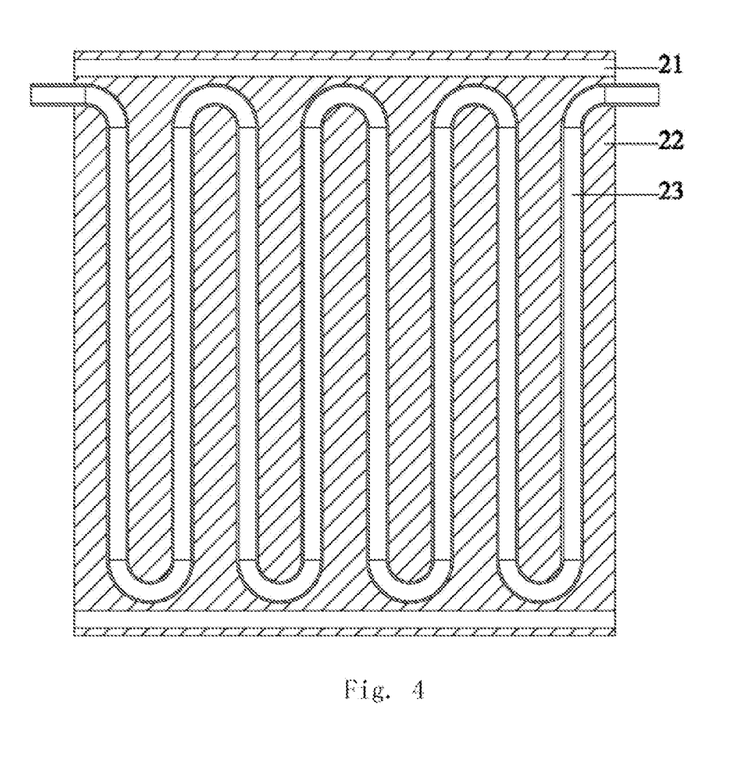
FIG. 4 is a structural cross-section view of a gas buffering chamber in a module for sampling, separating and enriching a detected object.
Figure 5:
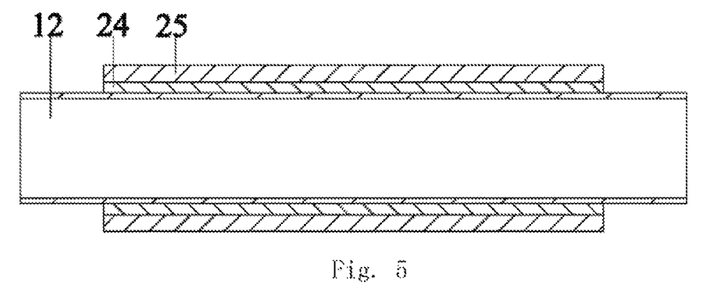
FIG. 5 is a structural cross-section view of a VOCs enriching device in a module for sampling, separating and enriching a detected object.

The components of the module for sampling, separating and enriching a detected object involved in the working process comprise the disposable mouthpiece 1, the saliva collector 2, the inspiration check valve 3, the expiration check valve 4, the first three-way solenoid valve 5, the second three-way solenoid valve 6, the activated carbon filter 7, the inlet check valve 8, the gas buffering chamber 9, the third three-way solenoid valve 10, the gas outlet 11, the adsorption tube 12, and the miniature vacuum pump 13. The expiration check valve 4 is connected to the second three-way solenoid valve 6 via the first three-way solenoid valve 5, the first three-way solenoid valve 5 is connected to the gas buffering chamber 9 via the second three-way solenoid valve 6, and the gas buffering chamber 9 is connected to the gas outlet 11 via the third three-way solenoid valve 10. The gas buffering chamber 9 will be heated to 100~150° C. by a heating rod (as shown in FIG. 4) if needed, and at the same time, the cooling plates on both sides of the VOCs adsorption tube 12 (as shown in FIG. 5) makes the adsorption tube 12 to a constant temperature of 20° C., thereby ensuring that the adsorption material has a comparatively large breakthrough volume value for the VOCs at the current temperature; when the temperature inside the gas buffering chamber 9 reaches a set value, the subject takes a deep breath, exhales towards the collecting device through the disposable mouthpiece 1, and at this point the exhaled breath will pass through the following pathways: the disposable mouthpiece 1→the expiration check valve 4→the first three-way solenoid valve 5→the second three-way solenoid valve 6→the gas buffering chamber 9→the third three-way solenoid valve 10→the gas outlet 11, and the gas buffering chamber 9 will keep the last 350 mL gas in the exhaled breath within its elongated stainless conduit 23.

FIG. 3 shows a working process in which the module for sampling, separating and enriching a detected object collects EBCs and enriches VOCs from the exhaled breath.

The components of the module for sampling, separating and enriching a detected object involved in the working process comprise the disposable mouthpiece 1, the saliva collector 2, the inspiration check valve 3, the expiration check valve 4, the first three-way solenoid valve 5, the second three-way solenoid valve 6, the activated carbon filter 7, the inlet check valve 8, the gas buffering chamber 9, the third three-way solenoid valve 10, the gas outlet 11, the adsorption tube 12, the miniature vacuum pump 13, the gas mass flow meter 14, the linear stepping motor 15, the piston 16, the washing liquid storage for condensation tube 17, the peristaltic pump 18, the condensation module 19, and the condensate collector 20. The expiration check valve 4 is connected with the gas mass flow meter 14 via the first three-way solenoid valve 5, the activated carbon filter 7 is connected with the gas buffering chamber 9 via the second three-way solenoid valve 6, and the gas buffering chamber 9 is communicated with the adsorption tube 12 via the third three-way solenoid valve 10. When the temperature of the adsorption tube 12 decreases to a set value, the miniature vacuum pump 13 start to work a set pumping speed, at this point a carrier gas (clean air) will pass through the following pathway: the inlet check valve 8→the activated carbon filter 7→the second three-way solenoid valve 6→the gas buffering chamber 9→the third three-way solenoid valve 10→the adsorption tube 12→the miniature vacuum pump 13, and in this way the 350 mL exhaled breath kept within the gas buffering chamber 9 will pass through the enriching material of the adsorption tube 12 gradually along with the carrier gas, and be adsorbed by the adsorption material and condensed under a condition of a lower temperature. So, the adsorption tube 12 enriches the VOCs gas molecules from the subject exhaled breath with the anatomical dead space removed. The adsorption tube 12 is then placed in an environment of 200° C., to cause the VOCs molecules to be desorbed from the enriching material and enter the subsequent separating and detection module.

Figure 6:
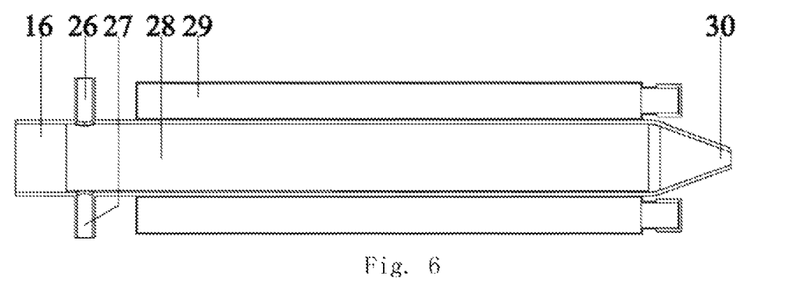
FIG. 6 is a structural cross-section view of a condensation module in a module for sampling, separating and enriching a detected object.

Synchronously with the enrichment of the VOCs, the subject exhales more breath, and at this point the exhaled breath pass through the following pathway: the disposable mouthpiece 1→the expiration check valve 4→the first three-way solenoid valve 5→the gas mass flow meter 14→the condensation module 19. A microcontroller will first read a temperature value from an ice cooling box 29 (as shown in FIG. 6) coating a condensation tube 28 at the periphery, wherein in order to guarantee the efficiency and repeatability of the operation of the system sampling condensate samples, the condensation temperature is usually suggested to be −5° C.~−10° C. Then, the microcontroller will read a flow value from the gas mass flow meter 14 and obtain the overall volume of the gas exhaled into the condensation tube. When reaching the required set overall volume of the exhaled gas, the linear stepping motor 15 will start to work and drive the piston 16, to make droplets agglutinated on the wall of the condensation tube to enter the condensate collector 20 for sampling and analysis by a subsequent detection module. After the agglutination and collection of one sample is finished, the peristaltic pump 18 starts to work and pumps the washing liquid into the condensation tube 28, and after a back and forth sliding of the piston 16, the cleaning work is done.

The above two steps are performed alternately to increase the collection efficiency of the exhaled breath collecting instrument.

As shown in FIG. 4, the gas buffering chamber 9 comprises a heating rod 21, a heating piece 22 and a conduit 23, in which both the heating rod 21 and the conduit 23 are placed within the heating piece 22. The working principle of the gas buffering chamber 9 is as follows. In operation, the heating rod 21 propagates heat to the whole heating piece 22 made of aluminium, ensuring that the temperature of the conduit 23 made of stainless steel located in the heating piece 22 is at 100° C.~150° C., thereby reducing the condensation loss of the 350 mL exhaled breath buffered in the conduit 23 on the inner wall.

As shown in FIG. 5, the module for sampling, separating and enriching a detected object also comprises an aluminium piece 24 and a cooling plate 25 to aid the adsorption tube 12 to finish enrichment of VOCs. The aluminium piece 24 is in close contact with the periphery of the adsorption tube 12, and the semiconductor cooling plate 25 is fixed on the outside of the aluminium piece 24. The working principle of this part is as follows. At the beginning of the VOCs enrichment, the semiconductor cooling plate 25 controls the temperature of the aluminium piece 24 to be maintained at 20° C., such that the temperature of the adsorption tube 12 is also maintained at 20° C., the adsorption quantity of the VOCs in the exhaled breath by the adsorption tube 12 is increased, and the repeatability of the enrichment of the adsorption tube 12 is also guaranteed.

As shown in FIG. 6, the condensation module 19 comprises the piston 16, the gas inlet 26, the inlet for washing liquid 27, the condensation tube 28, the ice cooling box 29, and the condensate outlet 30. The gas inlet 26, the inlet for washing liquid 27, the condensate outlet 30 and the condensation tube 28 are formed integrally, the piston 16 is inserted into the condensation tube 28, and the ice cooling box 29 is in close contact with the outside of the condensation tube 28. The working principle of the condensation module 19 is as follows. At the beginning of the EBCs collection, the temperature of the condensation tube 28 decreases to −5° C.~−10° C. by the ice crystals in the ice cooling box 29; the exhaled breath is passed into the condensation tube 28 via the gas inlet 26, condensed, and forms small droplets on the wall of the tube; the piston 16 slides 3~5 times back and forth along the tube wall of the condensation tube 28 under the drive of an outer push rod, and the tiny droplets previously condensed on the tube wall gather into larger droplets at the condensate outlet 30, and then will be collected by the condensate collector 20 in FIG. 3. Each time when the EBCs collection is finished, washing liquid for the condensation tube will come into the condensation tube 28 via the inlet for washing liquid 27, and the piston 16 will slide back and forth again, so the residues remaining on the tube wall of the condensation tube 28 will be cleaned, thereby preparing for the EBCs collection next time.

Figure 7:
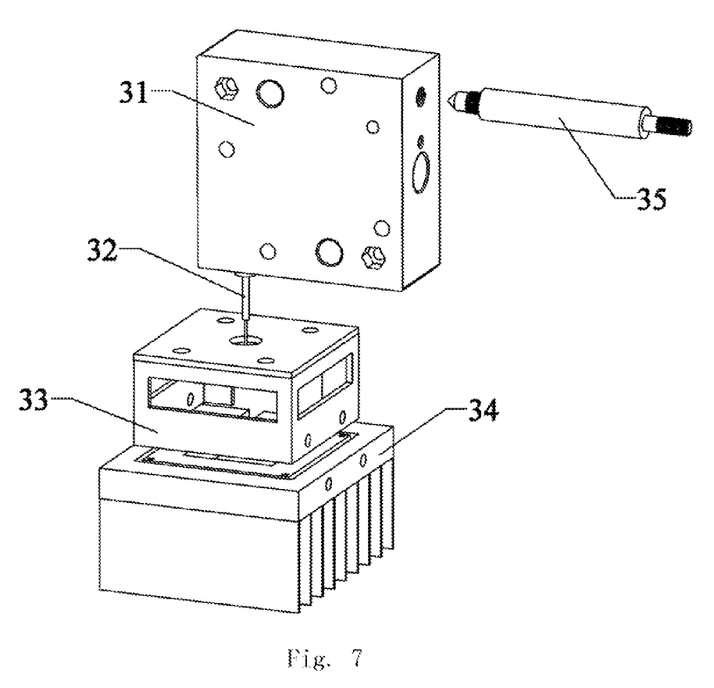
FIG. 7 is a structural schematic diagram of a combined VOCs detection module.

As shown in FIG. 7, the combined VOCs detection module comprises an outlet heating piece 31, a gas nozzle 32, an upper cover of sensor gas-chamber 33, a heat sink 34, and a conduit for capillary extraction 35. The gas nozzle 32 and the conduit for capillary extraction 35 are respectively in a direct threaded connection with the outlet heating piece 31, the upper cover of sensor gas-chamber 33 is snap-fitted with the heat sink 34, the upper cover of sensor gas-chamber 33 is connected with the outlet heating piece 31, and the gas nozzle 32 extends into the upper cover of sensor gas-chamber 33.

The capillary separation column is led out by the conduit for capillary extraction 35 and connected to the outlet heating piece 31 to ensure that the VOCs in the capillaries are kept in a high temperature state, the upper cover of sensor gas-chamber 33 is fixed with the outlet heating piece 31 via the gas chamber fixing hole 49, and the upper cover of sensor gas-chamber 33 and the heat sink 34 are connected via the first gas chamber closing hole 51 and the second gas chamber closing hole 56 and constitute a closed gas chamber, thereby ensuring that the sensor works in a condition with a steady gas flow. The capillary separation column protrudes out from a cambered guiding groove for capillary 41 in the outlet heating piece 31 into the gas nozzle 32, and is accurately aligned by the fixation of the relative position between the gas nozzle 32 and the sensor in the gas chamber.

Figure 8:
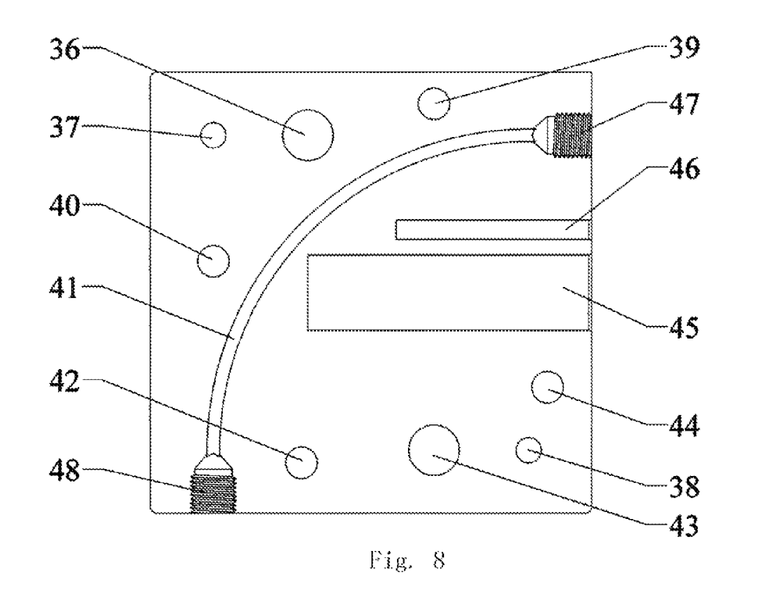
FIG. 8 is a structural schematic diagram of a separated outlet heating piece.

FIG. 8 shows the structure of the outlet heating piece 31, which employs a separated structure, and comprises a first perforation for hanging and fixing 36, a first screw perforation for heating piece incorporating 37, a second screw perforation for heating piece incorporating 38, a first pin perforation for heating piece 39, a second pin perforation for heating piece 40, the cambered guiding groove for capillary 41, a third pin perforation for heating piece 42, a second perforation for hanging and fixing 43, a fourth pin perforation for heating piece 44, a slot for heating rod 45, a slot for platinum resistor 46, a first insertion screw hole 47, and a second insertion screw hole 48. The separated outlet heating piece is formed by fitting two identical structures, and one of them is shown in FIG. 8. The relative position of the two heating pieces is fixed by adding pins into the four heating piece pin perforations 39, 40, 42, 44, and then the two heating pieces are combined as a whole by screwing screws into the heating piece incorporating screw perforations 37, 38. Two perforations for hanging and fixing 36, 43 fix the position of the outlet heating piece in the instrument. Two insertion screw holes 47, 48 connect the heating piece, the conduit for capillary extraction 35 and the gas nozzle 32. The cambered guiding groove for capillary 41 leads the capillary separation column to the gas nozzle 32 from the vertical direction.

A heating rod and a platinum resistor are inserted into the slot for heating rod 45 and the slot for platinum resistor 46 respectively, thereby realizing the measurement and control of the outlet temperature. When the heating rod and the platinum resistor need to be replaced, they can be conveniently taken out from their respective slots after separating the two heating pieces, if they have expanded and been clamped.

Figure 9:
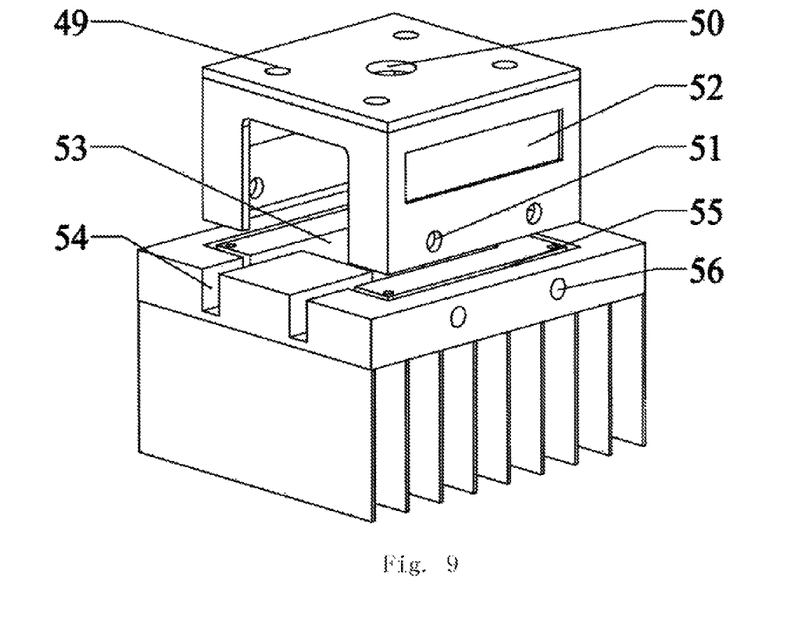
FIG. 9 is a structural schematic diagram of a snap-fit gas chamber.

As shown in FIG. 9, the gas chamber which consists of the upper cover of sensor gas-chamber 33 and the heat sink 34 comprises the gas chamber fixing holes 49, a gas chamber top hole 50, the first gas chamber closing hole 51, observation holes 52, a groove for cooling plate 53, groove for the lead wire of cooling plates 54, gas chamber embedding grooves 55, and the second gas chamber closing holes 56. The four centrosymmetric gas chamber fixing holes 49 fix the relative position of the upper cover of sensor gas-chamber 33 and the outlet heating piece 31, the upper cover of sensor gas-chamber 33 is snapped into the gas chamber embedding groove 55, the fixation of the gas chamber and the heat sink 34 is achieved via the gas chamber closing holes 51, 56, and the gas nozzle 32 enters the gas chamber via the outlet of the gas nozzle, and makes the capillary separation column aim to the sensitive region of the sensor.

A semiconductor cooling plate is placed in the groove for cooling plate 53 to control the working temperature of the sensor, and a wire leads out from the groove for the lead wire of cooling plate 54 to an external circuit. The heat generated when the cooling plate controls the temperature is conducted to the external environment through the heat sink 34. The observation holes 52 are disposed around the gas chamber so that the working state of the sensor and circuit can be observed. The frequency signal generated by the sensor is led via a signal interface to an external frequency count circuit for measurement.

Figure 10:
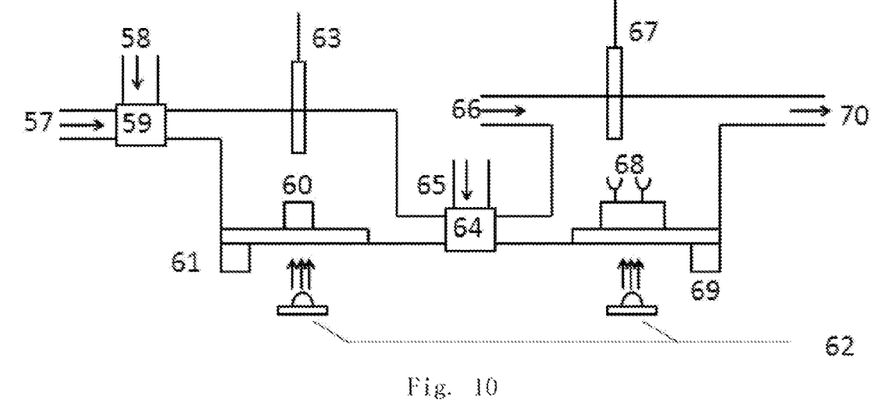
FIG. 10 is a structural schematic diagram of an EBCs detection module.

The structure of the EBCs detection module is as shown in FIG. 10, comprising an EBC inlet 57, an inlet for washing liquid 58, a first three-way valve 59, a composite LAPS sensor for heavy metal ions 60, a first working electrode 61, a light source controlled by a signal generating circuit 62, a reference electrode 63, a second three-way valve 64, a urea inlet 65, an inlet for CEA antibody-urease compounds 66, a detecting electrode 67, a CEA-LAPS sensor 68, a second working electrode 69, an outlet for waste liquid 70, a $Cr^{3+}$ ion detecting cavity and a CEA detecting cavity.

Therein, the EBC inlet 57, the inlet for washing liquid 58 and the $Cr^{3+}$ ion detecting cavity are connected via the first three-way valve 59, the urea inlet 65, the $Cr^{3+}$ ion detecting cavity and the CEA detecting cavity are connected via the second three-way valve 64, the reference electrode 63 is inserted into the $Cr^{3+}$ ion detecting cavity from its top, the composite LAPS sensor for heavy metal ions 60 and the first working electrode 61 are fixed to the bottom of the $Cr^{3+}$ ion detecting cavity, the first working electrode 61 is joined with the bottom of the composite LAPS sensor for heavy metal ions 60, the detecting electrode 67 is inserted into the CEA detecting cavity from its top, the CEA-LAPS sensor 68 and the second working electrode 69 are fixed to the bottom of the CEA detecting cavity, and the second working electrode 69 is joined with the bottom of the CEA-LAPS sensor 68. At the upper portion of the CEA detecting cavity are disposed the inlet for CEA antibody-urease compound liquid 66 and the outlet for waste liquid 70. One light source controlled by a signal generating circuit 62 is placed at a position corresponding to the composite LAPS sensor for heavy metal ions 60 under the $Cr^{3+}$ ion detecting cavity, and another light source controlled by a signal generating circuit 62 is placed at a position corresponding to the CEA-LAPS sensor 68 under the CEA detecting cavity.

A particular working process is as follows. The surface of the composite LAPS sensor for heavy metal ions 60 is prepared by employing the pulse laser deposition (PLD) and the material sensitive to heavy metal ions ($Cr^{3+}$) is made; the CEA-LAPS sensor is prepared by employing the chemical vapor deposition (CVD) and the material sensitive to $H^+$ is made, then the further immunologically modification could be carried out.

The human exhaled breath condensate is passed into the EBC detection module via the EBC inlet 57, and at the same time the composite LAPS sensor for heavy metal ions 60 starts to work and obtains the content of $Cr^{3+}$ ions in the condensate by detection. Then, the second three-way valve 64 is opened and the condensate is passed into the CEA detecting cavity. At this point, the CEA antibody-urease 78 compounds inflow via the inlet for CEA antibody-urease compound 66, are bonded with the CEA antigen 77 in the condensate, and form a sandwich structure with the CEA antibody-avidin 79, which is affixed to the CEA-LAPS sensor 68. Then, the washing liquid is passed into the cavity via the inlet for washing liquid 58 and cleans free compounds. Then, the urea is passed into the CEA detecting cavity via the urea inlet 65, reacts with the urease in the compound structure on the sensor, and leads to a change in pH, and the change in pH is related with the amount of the CEA antigen 77 in the condensate. Thereafter, the CEA-LAPS sensor 68 detects the change in pH, and finally the amount of the CEA antigen in the condensate is obtained.

Figure 11:
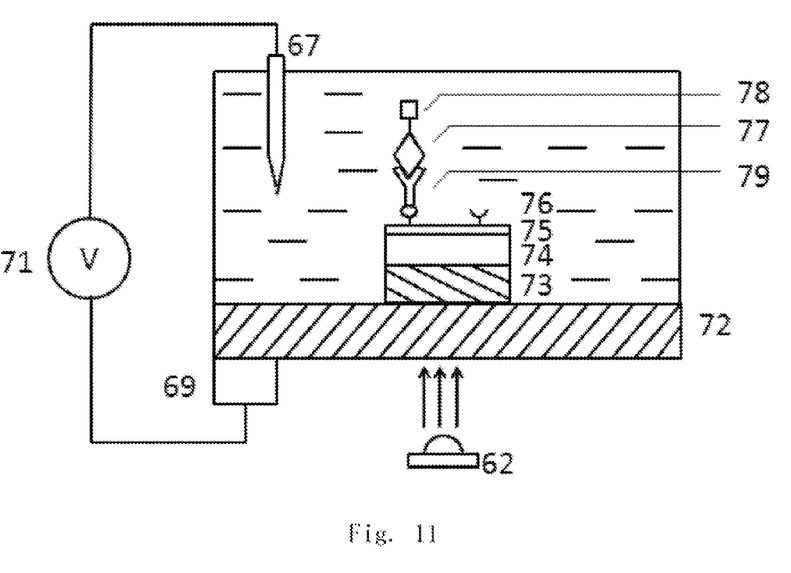
FIG. 11 is a structural schematic diagram of a CEA detecting cavity.

As shown in FIG. 11, the CEA-LAPS sensor 68 consists of a Si substrate 72, a $SiO_2$ layer 73, a $Si_3N_4$ film 74, a nanolayer 75, and a biotin layer 76. The $SiO_2$ layer 73 and the $Si_3N_4$ film 74 are in turn deposited on the Si substrate 72 by the chemical vapor deposition and the photolithography, and the nanolayer 75 and the biotin layer 76 are formed on the surface of the $Si_3N_4$ film 74 by the chemical coating method. Both the detecting electrode 67 and the second working electrode 69 are connected with a bias voltage 71.

A particular working process is as follows. On the surface of the CEA-LAPS sensor 68 are disposed the nanolayer 75 and the biotin layer 76. At this point, the condensate flows into the CEA detecting cavity, the CEA antigen 77 in the condensate bonds with the biotin layer 76 via a covalent bond, and affixs to the surface of the CEA-LAPS sensor 68. Then, the CEA antibody-avidin 79 and the CEA antibody-urease 78 flow into the CEA detecting cavity, and bonded with the CEA antigen 77, forming a sandwich structure as shown in the figure. Then, the washing liquid cleans out extra CEA antibody-urease 78, and only leaves the sandwich structure consisting of the CEA antigen 77, the CEA antibody-urease 78 and the CEA antibody-avidin 79 on the CEA-LAPS sensor 68 in the CEA detecting cavity. Then, the urea flows into the CEA detecting cavity, reacts with the urease on the sandwich structure, and leads to a change of pH, and the change in pH is related with the amount of the CEA antigen 77 in the condensate. The CEA-LAPS sensor 68 obtains the amount of the CEA antigen 77 in the condensate by detecting the change of pH.

The invention claimed is:

1. An integrated analysis device for simultaneously detecting human exhaled breath condensates (EBCs) and volatile organic compounds (VOCs) in human exhaled breath, comprising a module for sampling, separating and enriching a detected object, an EBCs detection module and a combined VOCs detection module; the module for sampling, separating and enriching the detected object is connected with the EBCs detection module via a syringe pump for sample injection, and the module for sampling, separating and enriching the detected object is connected with the combined VOCs detection module via a capillary separation column; wherein the EBCs detection module comprises an EBC inlet (57), an inlet for washing liquid (58), a first three-way valve (59), a composite light addressable potentiometric sensor (LAPS) for heavy metal ions ($Cr^{3+}$) (60), a first working electrode (61), a light source controlled by a signal generating circuit (62), a reference electrode (63), a second three-way valve (64), a urea inlet (65), a detecting electrode (67), a carcinoembryonic antigen light addressable potentiometric sensor (CEA-LAPS) (68), a second working electrode (69), a $Cr^{3+}$ ion detecting cavity and a carcinoembryonic antigen (CEA) detecting cavity; the EBC inlet (57), the inlet for washing liquid (58) and the $Cr^{3+}$ ion detecting cavity are connected via the first three-way valve (59); the urea inlet (65), the $Cr^{3+}$ ion detecting cavity and the CEA detecting cavity are connected via the second three-way valve (64); the reference electrode (63) is inserted into the $Cr^{3+}$ ion detecting cavity from its top; the composite LAPS for heavy metal ions ($Cr^{3+}$) (60) and the first working electrode (61) are fixed to the bottom of the $Cr^{3+}$ ion detecting cavity; the first working electrode (61) is joined with the bottom of the composite LAPS for heavy metal ions ($Cr^{3+}$) (60); the detecting electrode (67) is inserted into the CEA detecting cavity from its top; the CEA-LAPS (68) and the second working electrode (69) are fixed to the bottom of the CEA detecting cavity, and the second working electrode (69) is joined with the bottom of the CEA-LAPS (68); at the upper portion of the CEA detecting cavity are disposed an inlet for CEA antibody-urease compound liquid (66) and an outlet for waste liquid (70); one light source controlled by the signal generating circuit (62) is placed at a position corresponding to the composite LAPS for heavy metal ions ($Cr^{3+}$) (60) under the $Cr^{3+}$ ion detecting cavity, and another light source controlled by the signal generating circuit (62) is placed at a position corresponding to the CEA-LAPS (68) under the CEA detecting cavity.

2. The integrated analysis device for simultaneously detecting EBCs and VOCs in human exhaled breath according to claim 1, wherein the CEA-LAPS (68) is built by depositing a silicon dioxide ($SiO_2$) layer (73) and a silicon nitride ($Si_3N_4$) film (74) in turn on a Si substrate (72) a chemical vapor deposition and photolithography, and forming a nanolayer (75) and a biotin layer (76) on the surface of the $Si_3N_4$ film (74) by a chemical coating method.

3. The integrated analysis device for simultaneously detecting EBCs and VOCs in human exhaled breath according to claim 1, the module for sampling, separating and enriching the detected object further comprising a mouthpiece (1), a saliva collector (2), an inspiration check valve (3), an expiration check valve (4), a first three-way solenoid valve (5), a second three-way solenoid valve (6), an activated carbon filter (7), an inlet check valve (8), a gas buffering chamber (9), a third three-way solenoid valve (10), a gas outlet (11), an adsorption tube (12), a miniature vacuum pump (13), a gas mass flow meter (14), a linear stepping motor (15), a piston (16), a washing liquid storage for condensation tube (17), a peristaltic pump (18), a condensation module (19), and a condensate collector (20); wherein the mouthpiece (1) is connected with the first three-way solenoid valve (5) via the inspiration check valve (3) and the expiration check valve (4) in turn, the saliva collector (2) is connected between the mouthpiece (1) and the inspiration check valve (3), the two outlets of the first three-way solenoid valve (5) are connected respectively with the second three-way solenoid valve (6) and the gas mass flow meter (14); the inlet check valve (8) is then connected with the third three-way solenoid valve (10) via the activated carbon filter (7), the second three-way solenoid valve (6) and the gas buffering chamber (9) in turn, the two outlets of the third three-way solenoid valve (10) is then connected respectively with the gas outlet (11) and the adsorption tube (12) and to the miniature vacuum pump (13); the gas mass flow meter (14) is connected with the condensation module (19), and all the above connections are a gas pipeline connection; the washing liquid storage for condensation tube (17) is connected with the condensate collector (20) in a liquid pipeline via the peristaltic pump (18) and the condensation module (19) in turn; the linear stepping motor (15) is connected with the piston (16), and drives the piston (16) into the condensation module (19).

4. The integrated analysis device for simultaneously detecting EBCs and VOCs in human exhaled breath according to claim 3, the gas buffering chamber (9) further comprising a heating rod (21), a heating piece (22) and a conduit (23), wherein both the heating rod (21) and the conduit (23) are placed within the heating piece (22).

5. The integrated analysis device for simultaneously detecting EBCs and VOCs in human exhaled breath according to claim 3, the condensation module (19) further comprising the piston (16), a gas inlet (26), an inlet for washing liquid (27), a condensation tube (28), an ice cooling box (29), and a condensate outlet (30); the gas inlet (26), the inlet for washing liquid (27), the condensate outlet (30) and a condensation tube (28) are formed integrally, the piston (16) is inserted into the condensation tube (28), and the ice cooling box (29) is in close contact with the outside of the condensation tube (28).

6. The integrated analysis device for simultaneously detecting EBCs and VOCs in human exhaled breath according to claim 3, the module for sampling, separating and enriching the detected object further comprising an aluminium piece (24) and a cooling plate (25), the aluminium piece (24) is in close contact with the periphery of the adsorption tube (12), and the outside of the aluminium piece (24) is fixed with the semiconductor cooling plate (25).

7. The integrated analysis device for simultaneously detecting EBCs and VOCs in human exhaled breath according to claim 1, the combined VOCs detection module further comprising an outlet heating piece (31), a gas nozzle (32), a upper cover of sensor gaschamber (33), a heat sink (34), and a conduit for capillary extraction (35); the gas nozzle (32) and the conduit for capillary extraction (35) are respectively in a direct threaded connection with the outlet heating piece (31), the upper cover of sensor gas-chamber (33) is snap-fitted with the heat sink (34), the upper cover of sensor gas-chamber (33) is connected with the outlet heating piece (31), and the gas nozzle (32) extends into the upper cover of sensor gaschamber (33).

8. The integrated analysis device for simultaneously detecting EBCs and VOCs in human exhaled breath according to claim 7, the outlet heating piece (31) further comprising a cambered guiding groove for capillary (41), a slot for heating rod (45), a slot for platinum resistor (46), a first insertion screw hole (47), and a second insertion screw hole (48), a heating rod and a platinum resistor; the two ends of the cambered guiding groove for capillary (41) are respectively connected with the first insertion screw hole (47) and the second insertion screw hole (48), and the heating rod and the platinum resistor are respectively inserted into the slot for heating rod (45) and the slot for platinum resistor (46).

\* \* \* \* \*